(12) United States Patent
Chin et al.

(10) Patent No.: US 8,986,189 B2
(45) Date of Patent: Mar. 24, 2015

(54) METHOD AND APPARATUS FOR CLOSING OFF A PORTION OF A HEART VENTRICLE

(75) Inventors: Sing-Fatt Chin, Pleasanton, CA (US); Lon S. Annest, Tacoma, WA (US)

(73) Assignee: BioVentrix, Inc., San Ramon, CA (US)

( * ) Notice: Subject to any disclaimer, the term of this patent is extended or adjusted under 35 U.S.C. 154(b) by 0 days.

(21) Appl. No.: 12/828,974

(22) Filed: Jul. 1, 2010

(65) Prior Publication Data

US 2010/0268020 A1   Oct. 21, 2010

Related U.S. Application Data

(62) Division of application No. 11/450,131, filed on Jun. 8, 2006, now Pat. No. 7,766,816.

(60) Provisional application No. 60/689,012, filed on Jun. 9, 2005.

(51) Int. Cl.
| | |
|---|---|
| *A61F 2/00* | (2006.01) |
| *A61M 25/10* | (2013.01) |
| *A61B 17/04* | (2006.01) |
| *A61B 17/06* | (2006.01) |
| *A61B 17/00* | (2006.01) |
| *A61B 17/22* | (2006.01) |

(52) U.S. Cl.
CPC ........ *A61M 25/1011* (2013.01); *A61B 17/0401* (2013.01); *A61B 17/0469* (2013.01); *A61B 17/06166* (2013.01); *A61B 2017/00243* (2013.01); *A61B 2017/0404* (2013.01); *A61B 2017/0417* (2013.01); *A61B 2017/06028* (2013.01); *A61B 2017/061* (2013.01); *A61B 2017/06176* (2013.01); *A61B 2017/22054* (2013.01); *A61B 2017/22067* (2013.01)
USPC .......................................................... 600/37

(58) Field of Classification Search
USPC ......... 600/16–18, 37; 128/897, 899; 606/213, 606/148, 232
See application file for complete search history.

(56) References Cited

U.S. PATENT DOCUMENTS

| | | | |
|---|---|---|---|
| 4,007,743 A | * | 2/1977 | Blake ............................ 606/232 |
| 5,295,958 A | | 3/1994 | Shturman |

(Continued)

FOREIGN PATENT DOCUMENTS

| | | |
|---|---|---|
| EP | 1 078 644 A1 | 2/2001 |
| WO | 00/06028 A1 | 2/2000 |

(Continued)

OTHER PUBLICATIONS

European Examination Report of EP Patent Application 05810316.9 dated Mar. 10, 2009, 6 pages.

(Continued)

*Primary Examiner* — Christine Matthews
(74) *Attorney, Agent, or Firm* — Kilpatrick Townsend & Stockton LLP

(57) ABSTRACT

Apparatus and methods to reduce ventricular volume are disclosed. The device takes the form of a transventricular anchor, which presses a portion of the ventricular wall inward, thereby reducing the available volume of the ventricle. The anchor is deployed using a curved introducer that may be inserted into one ventricle, through the septum and into the opposite ventricle. Barbs or protrusions along the anchor body combined with a mechanical stop and a sealing member hold the device in place once deployed.

7 Claims, 3 Drawing Sheets

(56) References Cited

U.S. PATENT DOCUMENTS

| | | | |
|---|---|---|---|
| 5,830,224 A | 11/1998 | Cohn et al. | |
| 5,961,440 A | 10/1999 | Schweich, Jr. et al. | |
| 6,045,497 A | 4/2000 | Schweich et al. | |
| 6,050,936 A | 4/2000 | Schweich, Jr. et al. | |
| 6,059,715 A | 5/2000 | Schweich, Jr. et al. | |
| 6,125,852 A | 10/2000 | Stevens et al. | |
| 6,162,168 A | 12/2000 | Schweich, Jr. et al. | |
| 6,165,119 A | 12/2000 | Schweich, Jr. et al. | |
| 6,165,120 A | 12/2000 | Schweich, Jr. et al. | |
| 6,258,021 B1 | 7/2001 | Wilk | |
| 6,260,552 B1 | 7/2001 | Mortier et al. | |
| 6,406,420 B1 | 6/2002 | McCarthy et al. | |
| 6,494,825 B1 | 12/2002 | Talpade | |
| 6,511,416 B1 | 1/2003 | Green et al. | |
| 6,572,529 B2 | 6/2003 | Wilk | |
| 6,616,684 B1 | 9/2003 | Vidlund et al. | |
| 6,705,988 B2 | 3/2004 | Spence et al. | |
| 6,709,382 B1 | 3/2004 | Horner | |
| 6,746,471 B2 | 6/2004 | Mortier et al. | |
| 6,776,754 B1 | 8/2004 | Wilk | |
| 6,808,488 B2 | 10/2004 | Mortier | |
| 6,859,662 B2 | 2/2005 | Bombardini | |
| 6,890,295 B2 | 5/2005 | Michels et al. | |
| 7,146,225 B2 | 12/2006 | Guenst et al. | |
| 7,326,177 B2 | 2/2008 | Williamson | |
| 7,390,329 B2 | 6/2008 | Westra et al. | |
| 7,722,523 B2 | 5/2010 | Mortier et al. | |
| 7,753,923 B2 * | 7/2010 | St. Goar et al. | 606/148 |
| 7,766,816 B2 | 8/2010 | Chin et al. | |
| 7,785,248 B2 | 8/2010 | Annest et al. | |
| 8,066,766 B2 | 11/2011 | To et al. | |
| 8,123,668 B2 | 2/2012 | Annest et al. | |
| 8,394,008 B2 | 3/2013 | Annest et al. | |
| 8,425,402 B2 | 4/2013 | Annest et al. | |
| 8,449,442 B2 | 5/2013 | Annest et al. | |
| 8,491,455 B2 | 7/2013 | Annest et al. | |
| 8,506,474 B2 | 8/2013 | Chin et al. | |
| 8,636,639 B2 | 1/2014 | Annest et al. | |
| 2001/0041821 A1 | 11/2001 | Wilk | |
| 2002/0058855 A1 | 5/2002 | Schweich, Jr. et al. | |
| 2002/0077524 A1 | 6/2002 | Schweich, Jr. et al. | |
| 2002/0120298 A1 | 8/2002 | Kramer et al. | |
| 2002/0123768 A1 | 9/2002 | Gilkerson et al. | |
| 2002/0169359 A1 | 11/2002 | McCarthy et al. | |
| 2002/0169360 A1 | 11/2002 | Taylor et al. | |
| 2002/0188170 A1 * | 12/2002 | Santamore et al. | 600/37 |
| 2003/0032979 A1 | 2/2003 | Mortier et al. | |
| 2003/0163165 A1 | 8/2003 | Bornzin et al. | |
| 2003/0166992 A1 | 9/2003 | Schweich, Jr. et al. | |
| 2003/0181951 A1 | 9/2003 | Cates | |
| 2004/0167580 A1 | 8/2004 | Mann et al. | |
| 2004/0225304 A1 | 11/2004 | Vidlund et al. | |
| 2005/0065506 A1 | 3/2005 | Phan | |
| 2005/0096498 A1 | 5/2005 | Houser et al. | |
| 2005/0137688 A1 | 6/2005 | Salahieh et al. | |
| 2005/0143620 A1 | 6/2005 | Mortier et al. | |
| 2005/0288613 A1 | 12/2005 | Heil, Jr. | |
| 2006/0135962 A1 | 6/2006 | Kick et al. | |
| 2006/0161040 A1 | 7/2006 | McCarthy et al. | |
| 2006/0161238 A1 | 7/2006 | Hall | |
| 2006/0200002 A1 | 9/2006 | Guenst | |
| 2006/0241340 A1 | 10/2006 | Schroeder et al. | |
| 2006/0247672 A1 | 11/2006 | Vidlund et al. | |
| 2006/0276684 A1 | 12/2006 | Speziali | |
| 2007/0010876 A1 | 1/2007 | Salahieh et al. | |
| 2007/0049971 A1 | 3/2007 | Chin et al. | |
| 2007/0055303 A1 | 3/2007 | Vidlund et al. | |
| 2007/0073274 A1 | 3/2007 | Chin et al. | |
| 2007/0112244 A1 | 5/2007 | McCarthy et al. | |
| 2007/0161846 A1 | 7/2007 | Nikolic et al. | |
| 2007/0203503 A1 | 8/2007 | Salahieh et al. | |
| 2008/0082132 A1 | 4/2008 | Annest et al. | |
| 2008/0097148 A1 | 4/2008 | Chin et al. | |
| 2008/0269551 A1 | 10/2008 | Annest et al. | |
| 2008/0294251 A1 | 11/2008 | Annest et al. | |
| 2009/0093670 A1 | 4/2009 | Annest et al. | |
| 2009/0270980 A1 | 10/2009 | Schroeder et al. | |
| 2010/0010538 A1 | 1/2010 | Juravic et al. | |
| 2010/0016655 A1 | 1/2010 | Annest et al. | |
| 2010/0057000 A1 | 3/2010 | Melsheimer et al. | |
| 2011/0160750 A1 | 6/2011 | Annest et al. | |
| 2012/0190958 A1 | 7/2012 | Annest et al. | |
| 2013/0090523 A1 | 4/2013 | Van Bladel et al. | |
| 2013/0090672 A1 | 4/2013 | Butler et al. | |
| 2013/0096579 A1 | 4/2013 | Annest et al. | |
| 2013/0324787 A1 | 12/2013 | Chin et al. | |
| 2013/0325041 A1 | 12/2013 | Annest et al. | |
| 2014/0031613 A1 | 1/2014 | Annest et al. | |
| 2014/0051916 A1 | 2/2014 | Chin et al. | |

FOREIGN PATENT DOCUMENTS

| | | |
|---|---|---|
| WO | 02/30335 A2 | 4/2002 |
| WO | 03/032818 A3 | 4/2003 |
| WO | 2005/092203 A1 | 10/2005 |
| WO | 2006/044467 A2 | 4/2006 |
| WO | 2007/022519 A2 | 2/2007 |

OTHER PUBLICATIONS

International Search Report and Written Opinion of PCT Application No. PCT/US06/32663, Jul. 31, 2007, 5 pages.
International Search Report and Written Opinion of PCT Application No. PCT/US2005/036690, mailed Jul. 9, 2007, 6 pages.
International Search Report and Written Opinion of PCT Application No. PCT/US09/51288, mailed Sep. 15, 2009, 9 pages.
International Search Report and Written Opinion of PCT Application No. PCT/US08/64255, mailed Sep. 29, 2008, 17 pages.
International Search Report and Written Opinion of PCT Application No. PCT/US06/22594, mailed Oct. 1, 2008, 9 pages.
International Search Report and Written Opinion of PCT Application No. PCT/US08/78810, mailed Feb. 12, 2009, 11 pages.
International Search Report and Written Opinion of PCT/US2012/058106, mailed Nov. 26, 2012, 14 pages.
International Search Report and Written Opinion of PCT/US2012/58176, mailed Jan. 8, 2013, 19 pages.
International Search Report and Written Opinion of PCT Application No. PCT/US12/58074, mailed Mar. 13, 2013, 18 pages.
International Search Report and Written Opinion of PCT/US2012/058182, mailed Mar. 1, 2013, 19 pages.
Extended European Examination Report of EP Patent Application 06802038.7 dated Nov. 12, 2013, 13 pages.
International Report on Patentability of PCT/US2012/058074 dated Apr. 10, 2014, 11 pages.
International Report on Patentability of PCT/US2012/058176 dated Apr. 10, 2014, 8 pages.

* cited by examiner

US 8,986,189 B2

METHOD AND APPARATUS FOR CLOSING OFF A PORTION OF A HEART VENTRICLE

CROSS-REFERENCES TO RELATED APPLICATIONS

The present application is a Divisional of U.S. Ser. No. 11/450,131 filed Jun. 8, 2006 (Allowed) which application claims the benefit of U.S. Provisional Application No. 60/689,012 filed Jun. 9, 2005; the full disclosures of which are incorporated herein by reference in their entirety.

FIELD OF THE INVENTION

The present invention relates to methods and apparatus for temporarily or permanently closing off a portion of the ventricle of the heart.

BACKGROUND OF THE INVENTION

In left ventricular hypertrophy, the myocardium of the left ventricle becomes thickened to the point of interfering with effective heart contraction. A surgical procedure for treating congestive heart failure, involves removing a triangular portion of a patient's heart. In this operation, approximately one-third of the patient's left ventricular muscle is removed. The result is that the smaller heart pumps more efficiently. This new technique of course requires open-heart surgery, with its attendant expense and extended convalescence.

One method to reduce ventricular volume is disclosed in U.S. Pat. No. 6,776,754 to Wilk, which is hereby incorporated by reference in its entirety.

For this and other potential procedures, it would be beneficial to have a method and system that could be temporarily and/or permanently implanted to close off a portion of the ventricle.

SUMMARY OF THE INVENTION

The present invention relates to a catheter or surgical based system capable of closing off a portion of a ventricle of a patient. The ventricle may be temporarily blocked during a surgical procedure or it may be permanently or semi-permanently closed off to improve cardiac function.

The present invention takes the form of an anchor for performing heart reconstruction including an elongated body, a plurality of protrusions extending from the body, and first and second mechanical stops or sealing members attachable to the body.

The anchor of mechanical stop may include two or more folding arms. The folding arms may be pivotally attached to the first end of the body.

One end of the anchor may include a curved needle that forms one end of the anchor.

The anchor may be used with a curved introducer. The elongated body being sized and configured to pass through the curved introducer.

The second sealing member may be held in place by a plurality of protrusions.

The sealing member may be formed of a resilient material.

A method of performing ventricular reconstruction, including the steps: (a) passing a curved needle through an anterior wall of a left ventricle of a patient; (b) passing the curved needle through the septum and into the right ventricle; (c) inserting an anchor into the needle; (d) allowing one or more arms located on a distal end of said anchor to deploy; (e) removing the curved needle; (f) placing a sealing member over a proximal end of said anchor; (g) folding a wall of the ventricle inward; (h) and using the sealing member to hold the folded wall in place.

The method may include passing the curved needle through an anterior wall of the right ventricle prior to step (d).

The method may be used to reduce the volume of the left ventricle and/or to treat left ventricular hypertrophy.

The method may include using the sealing member to hold the wall of the ventricle in place by engaging one or more protrusions extending from the anchor.

The method using a sealing member formed of a resilient material, such that the sealing member is resiliently deformed, thereby resiliently pressing against the wall of the ventricle.

The method may include the step of removing a portion of the anchor after the wall of the ventricle has been moved.

The method may be used to temporarily or permanently implant the device.

DETAILED DESCRIPTION OF THE INVENTION

Figure 1A:
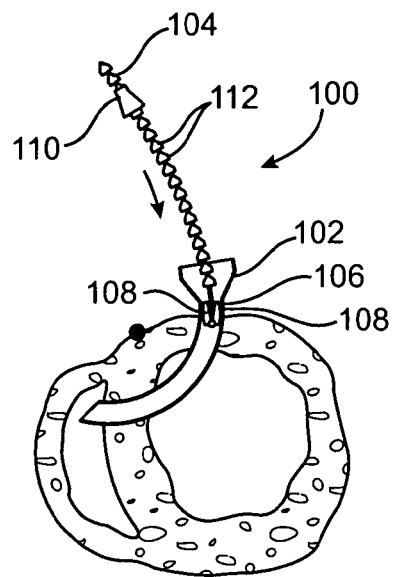
FIGS. 1A-1C show a method and device for left ventricular reconstruction using a left ventricular approach.
Figure 1B:
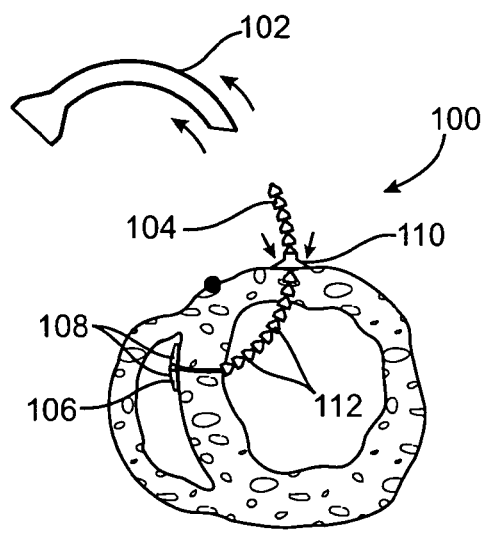
Figure 1C:
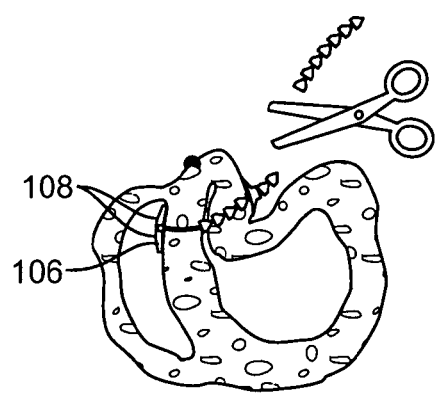

FIGS. 1A-1C show a method and device 100 for left ventricular reconstruction using a left ventricular approach. The device is an anchor deployment system 100, which is guided to the correct location on the heart by introducing a hollow curved introducer or needle 102 in through the anterior wall of the left ventricle. A visual guidance system, such as TEE, may be used to ensure the placement accuracy. The tip of the curved needle 102 is then guided through the septum and into the right ventricle. Either before placement or once the needle 102 is in place, the transventricular anchor 104 is loaded into the needle 102. The distal tip of the anchor 104 is extended into the cavity of the right ventricle.

The distal tip of the anchor 104 has a mechanical stop 106. Although it may take any suitable form, such as a resilient member or mechanical device, in the embodiment shown, the stop 106 has two or more pivoting arms 108. While the anchor 104 is within the needle 102, the arms 108 are held close to the body of the anchor 104. When the distal tip of the anchor 104 extends beyond the distal tip of the needle 102, the arms 108 are free to open. The arms 108 may be biased toward the open position or they maybe be manually opened. Once opened, the arms 108 prevent the distal end of the anchor 104 from passing back through the opening in the septum.

After the anchor 104 is in place, the needle 102 may be removed. A proximal sealing lock 110 is then slid onto the proximal end of the anchor 104. The sealing lock 110 is slid along the body and over one or more barbs 112 or other protrusions extending from the body of the anchor 104. The barbs 112 may take any suitable form, such as rounded or triangular. In the embodiment shown, the barbs 112 are generally triangular in shape. The proximal sealing lock 110 is advance until the anterior wall of the left ventricle is pressed inward, thereby folding the wall and reducing the interior volume of the left ventricle. Once the sealing lock 110 is advanced into place, the proximal portion of the body of the anchor 104 may be trimmed or cut off. Although the sealing lock 110 may be formed of any suitable material, the sealing lock 110 shown is made of a resilient material to allow it open and be compressed against the heart tissue. The resilience of the material provides benefits both in helping to seal the opening created as well has resiliently holding the wall of the ventricle in the modified configuration.

In alternate embodiments, an adhesive, bonding or other mechanical or chemical means may be used to connect the sealing lock 110 to the anchor 104.

If desired, the tip of the hollow needle 102 may be equipped with a pressure sensor to guide the practitioner to know if the tip is in the left ventricle, septum or the right ventricle by sensing the pressure. The hollow needle 102 may also be equipped with electrical sensor (EKG, Monophasic Action Potential) to sense if the puncture sight is the viable tissue or infracted tissue.

Figure 2A:
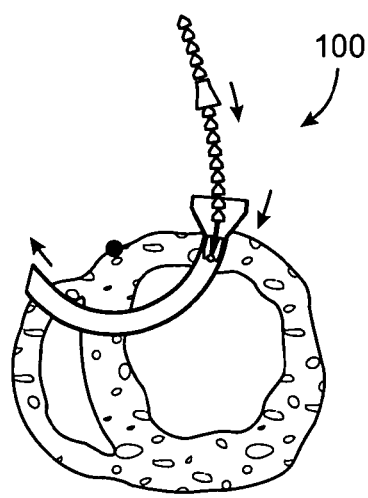
FIGS. 2A-C show an alternate procedure of FIGS. 1A-C.
Figure 2B:
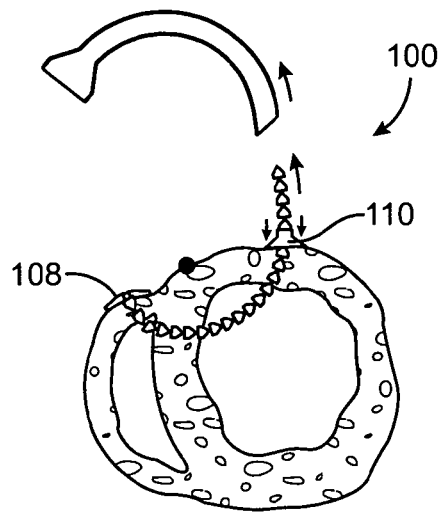
Figure 2C:
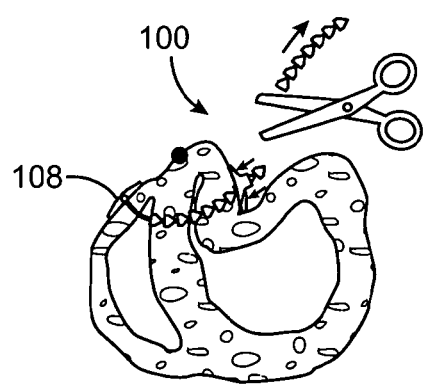

FIGS. 2A-C show an alternate procedure of that shown in FIGS. 1A-C. In this method, the distal end of the anchor is again guided to the anterior wall of the left ventricle. The tip of the curved needle 102 is then guided through the septum and into the right ventricle. In the configuration shown in FIG. 2A, the introducer 102 also extends through the anterior wall of the right ventricle. Once deployed, the distal tip of the anchor 104 is outside the right ventricle and the proximal tip is outside the left ventricle.

Figure 3A:
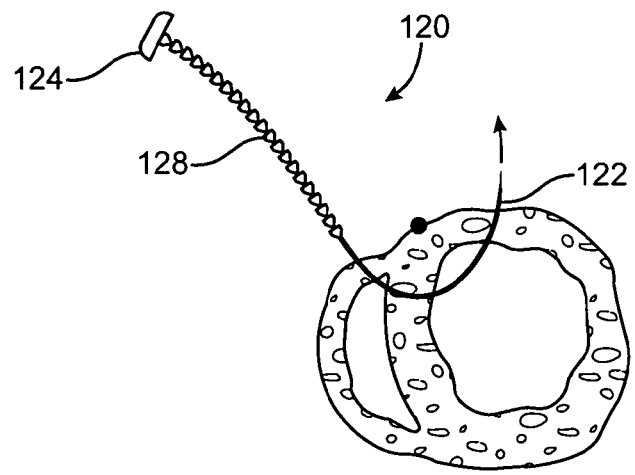
FIGS. 3A-B show a method and device for left ventricular reconstruction using a right ventricular approach.
Figure 3B:
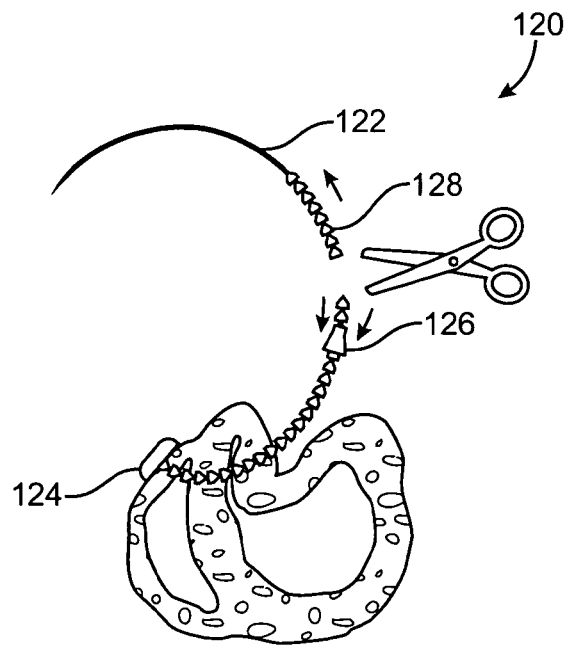

FIGS. 3A-B show a method and device for left ventricular reconstruction 120 using a right ventricular approach. In this version, a curved needle 122 forms the distal tip of the anchor. The curved needle 122 is inserted through the anterior wall and into the right ventricle, through the septum, and through the anterior wall of the left ventricle. The body of the anchor follows the curved needle 122 and is fed through until the proximal stop 124 engages the anterior surface of the right ventricle. The anterior wall of the left ventricle is pressed inward over the body of the anchor. A distal sealing stop 126 is threaded over the anchor 120 and slid in place against the anterior surface of the right ventricle. The heart tissue may be pressed inward to fold the wall of the heart prior to the placement of the sealing stop 126 or the sealing stop 126 may be used to manipulate the heart tissue. A plurality of barbs or protrusions 128 extend from the surface of the anchor body. The barbs 128 help hold the heart tissue in place. The curved needle 122 and the excess portion of the distal end of the anchor may be removed. This may be done before or after the distal sealing stop 126 has been placed.

The transventricular anchor may be temporarily or permanently implanted. A temporary implantation may be beneficial to test the effectiveness of the treatment for a particular patient. Other surgical procedures may only require a temporary reduction in ventricle volume. For these situations, the device may be removable. To remove the device, it may be cut or broken or another release mechanism may be used to allow for removal of the device. Once the efficacy is confirmed for a patient, a permanent version of the anchor could be implanted. Alternately, a semi-permanent or permanent device may be implanted initially.

The transventricular anchor may be used to treat medical conditions including left ventricular hypertrophy. While the examples given are specific to performance of reconfiguration of the left ventricle. Other procedures could also be performed to reduce the internal volume of other bodily structures, including other chambers of the heart, gastric system, etc.

The present invention may be deployed during an open-heart procedure or it may be one using minimally invasive techniques using catheter systems and/or ports formed between the ribs.

Many features have been listed with particular configurations, options, and embodiments. Anyone or more of the features described may be added to or combined with any of the other embodiments or other standard devices to create alternate combinations and embodiments.

Although the invention has been fully described above, in relation to various exemplary embodiments, various additions or other changes may be made to the described embodiments without departing from the scope of the present invention. Thus, the foregoing description has been provided for exemplary purposes only and should not be interpreted to limit the scope of the invention.

What is claimed is:

1. An anchor deployment system for performing heart reconstruction, the anchor deployment system comprising:
    an elongated body comprising a plurality of protrusions extending from said body, wherein each of the plurality of protrusions comprises a barb,
    a mechanical stop member attached to a first end of said body, said mechanical stop member comprising arms pivotally attached to said first end such that each arm pivots between a collapsed configuration and a deployed configuration, and
    a sealing member unconnected from the mechanical stop member and attachable to said body,
    wherein interaction between the sealing member and the plurality of protrusions facilitates movement of the sealing member along the elongated body toward the mechanical stop member and resists movement of the sealing member along the elongated body away from the mechanical stop member so as to permanently affix the sealing member about said body via the plurality of protrusions.

2. The anchor deployment system of claim 1, in combination with a curved introducer, said curved introducer being configured for insertion through a wall of said heart and said elongated body sized and configured to pass through said curved introducer.

3. The anchor deployment system of claim 1, wherein said sealing member is formed of a resilient material such that said sealing member is configured to seal an opening formed in a wall of said heart by said anchor deployment system.

4. The anchor deployment system of claim 1, wherein the barb of each of the plurality of protrusions comprises a triangular shape.

5. The anchor deployment system of claim 2, wherein said curved introducer comprises a pressure sensor configured to facilitate in determining a position of said curved introducer with respect to said heart by sensing a pressure.

6. The anchor deployment system of claim 2, wherein said curved introducer comprises an electrical sensor configured to sense if a puncture sight comprises viable tissue or infarcted tissue.

7. An anchor deployment system for performing heart reconstruction, the anchor deployment system comprising:
    an elongated body comprising a plurality of protrusions, wherein each of the plurality of protrusions comprises a barb,
    a mechanical stop member attached to a first end of said body, wherein said mechanical stop member is formed of arms, said arms being pivotally attached to said first end of said body and biased toward an open position such that each arm pivots from a closed position to the open position, and
    a sealing member unconnected from the mechanical stop member and attachable to said body, wherein the sealing member is moveable along the elongated body toward the mechanical stop member, and wherein the plurality of protrusions prevent movement of the sealing member along the elongated body away from the mechanical stop member such that the sealing member is permanently affixed about said body via the plurality of protrusions.

* * * * *